United States Patent [19]

Fujisaki et al.

[11] Patent Number: 4,485,095
[45] Date of Patent: Nov. 27, 1984

[54] PRONASE USED FOR THE TREATMENT OF DISEASES OF THE LIVER AND KIDNEYS IN HUMANS AND ANIMALS

[75] Inventors: Shigemi Fujisaki, Nishinomiya; Mitsuaki Mitani, Sagamihara, both of Japan

[73] Assignee: Kaken Pharmaceutical Co., Ltd., Japan

[21] Appl. No.: 405,770

[22] Filed: Aug. 6, 1982

[30] Foreign Application Priority Data

Aug. 10, 1981 [JP] Japan .............................. 56-125002

[51] Int. Cl.³ ............................................. A61K 37/48
[52] U.S. Cl. ...................................................... 424/94
[58] Field of Search ......................................... 424/94

[56] References Cited

U.S. PATENT DOCUMENTS

| | | | |
|---|---|---|---|
| 2,073,659 | 3/1937 | Stratton | 424/94 |
| 3,004,893 | 10/1961 | Martin | 424/94 |
| 3,268,409 | 8/1966 | Nomine et al. | 424/94 |
| 3,324,002 | 6/1967 | Antonides | 424/94 |
| 3,819,830 | 6/1974 | Yoshimura et al. | 424/94 |

OTHER PUBLICATIONS

Medicine and Drug Journal, pp. 2003–2009, vol. 15, No. 12 (1979) (plus translation).
Belloni et al.—Chem. Abst. vol. 71, (1969), p. 2053j.

*Primary Examiner*—Sam Rosen
*Attorney, Agent, or Firm*—Jacobs & Jacobs

[57] ABSTRACT

Diseases of the liver and kidneys in humans and animals may be prevented and treated by administering a therapeutically effective amount of a member selected from the group consisting of one or more proteolytic enzymes, one or more polysaccharide mucopolysaccharide-lysing enzymes, and mixtures thereof, in combination with a pharmaceutically acceptable carrier.

3 Claims, No Drawings

PRONASE USED FOR THE TREATMENT OF DISEASES OF THE LIVER AND KIDNEYS IN HUMANS AND ANIMALS

The present invention relates to agents useful for the prevention and treatment of diseases of the liver and kidneys in humans and animals.

Diseases of the liver and kidneys in humans and animals are well known. In recent years, however, diseases such as viral hepatitis and alcoholic hepatitis and the corresponding nephritis have increased among the human population which results in a significant social problem. In addition, there have been increasing cases of transitions of acute hepatitis to chronic hepatitis, from chronic hepatitis to hepatocirrhosis and from hepatocirrhosis to liver cancer. Similarly, an increasing number of cases have been observed of a transition from nephritis to renal insufficiency via chronic nephritis and nephrosis. It has, therefore, become increasingly important for saving human and animal lives as well as to cure these disorders, to treat these disorders at the inflammation stage to prevent their transition to cancer or renal insufficiency.

The present invention is based on the surprising discovery that one or more proteolytic enzymes and mixtures thereof are useful in the prevention and treatment of a broad range of diseases of the liver and kidneys in humans and animals. More particularly, the present invention comprises a therapeutically effective amount of a member selected from the group consisting of one or more proteolytic enzymes, one or more polysaccharide.mucopolysaccharide-lysing enzymes, and mixtures thereof, in combination with a pharmaceutically acceptable carrier.

Representative proteolytic enzymes useful according to the present invention are, for example, trypsin, α-chymotrypsin, bromelain, papain, serrathiopeptidase, seaprose, protease, streptokinase, proctase, pronase, prozyme, urokinase, pancreatin and fibrinolysin. Representative polysaccharide.mucopolysaccharide-lysing enzymes useful according to the present invention are, for example, α-amylase, lysozyme chloride and hyaluronidase. These enzymes may be used singly or in a combination of two or more. Pronase can be obtained by cultivating *Streptomyces griseus* by using procedures and techniques per se known in the field of cultivation of micro-organisms followed by the extraction and purification of the resulting culture broth to obtain the desired pronase.

The compositions according to the present invention may be administered orally, parenterally, for example by injection, and rectally. Thus, compositions according to the present invention include tablets, capsules, powders, granules and the like which may be prepared using techniques per se known in the pharmaceutical field in forms suitable for parenteral administration such as, for example, sterile solutions for injection which also may be prepared according to techniques and procedures per se known in the pharmaceutical field, as well as rectally administrable forms such as suppositories, ointments and the like. If desired, the active agent of the pharmaceutical compositions according to the present invention may be used in combination with other pharmaceuticals, particularly other compositions useful for treating diseases of the liver and kidneys, antibiotics, immunoactivators, antineopolastic agents and the like.

The present invention also includes a method of preventing and treating diseases of the liver and kidneys in humans and animals which comprises administering to a human or animal in need thereof, a therapeutically effective amount of a member selected from the group consisting of one or more proteolytic enzymes, one or more polysaccharide.mucopolysaccharide-lysing enzymes, and mixtures thereof, in combination with a pharmaceutically acceptable carrier. The dosage range will vary depending upon, among other things, the nature of the patient (human or animal), the weight, the age of the patient, past medical history, severity of the condition, route of administration, particular dosage form and the like. From 10–50,000 mg per day for an adult human has been found to be a suitable range for oral administration and 10–1,000 mg has been found to be a suitable range when the compositions of the present invention are formulated into enteric preparations, in the case of enzymes which are unstable in gastric juices. In terms of enzyme units of each enzyme, the oral dosage range should be from 20,000–400,000 serrathiopeptidase units in the case of serrathiopeptidase in an enteric preparation, 40,000–800,000 bromelain units in the case of bromelain, 20,000–800,000 units in the case of streptokinase, and 10,000–500,000 tyrosine units in the case of pronase. Similar dosage ranges would be used for other agents according to the present invention. A suitable range for animals would be from about 0.1 mg to about 15 mg per day.

Depending upon the particular enzymes used, it is generally preferred to formulate them into an enteric preparation and to administer them orally.

A particular advantage of the present invention lies in the fact that the proteolytic enzymes and the polysaccharide.mucopolysaccharide-lysing enzymes once they are absorbed are transmigrated in very large amounts to lesions of the liver and kidneys. We have also observed that the enzymes are carried to tissues which show subsidence of edema, infiltrate round cells, assist in the production of new blood vessels, dissolve fibrin, and promote an increase in polysaccharide—acid ones in particular. The enzymes are useful in treating chronic inflammation conditions of the liver and kidneys, such as retroplasia or abnormal proliferation.

The following non-limitative examples more particularly illustrate the present invention:

EXAMPLE 1

Onto a uniform mixture of 10 g of serrathiopeptidase, 190 g of lactose, and 70 g of potato starch is poured a 3% aqueous solution of hydroxypropylcellulose and the resulting mixture is kneaded. The mixture is granulated and with this granules is mixed 0.3% magnesium stearate. The resulting mixture is compressed into tablets.

EXAMPLE 2

To a mixture of 20 g of pronase and 40 g of lactose is added 10 g of hydroxypropylmethylcellulose. The resulting mixture is made into granules, which are uniformly coated with cellulose acetate phthalate to prepare enteric granules.

EXAMPLE 3

The pronase enteric granules obtained in Example 2 are filled into capsules to prepare capsule preparations.

CLINICAL EXAMPLE 1 male, 58 years old

Diagnosis: hepatocirrhosis, chronic hepatitis.

Chief complaint: anorexia, mild pressure sensation at the right hypochondriac region, general fatigue.

Present illness: The patient has had the foregoing symptoms since 2–3 years ago and was diagnosed as having hepatocirrhosis on May 24 at another hospital.

Present condition: There are observed no abnormalities except mild hypertrophy of the liver. Serum examinations and ultrasonography were made.

Ultrasonography: No abnormalities in both the kidneys; mild hypertrophy of the spleen; the gallbladder is in a state of large cysts and contains no gallstone; the choledochus has no dilatation; the pancreas has mild swelling and the surface thereof is smooth; no significant changes are observed inside the pancreas.

Liver: The surface is almost smooth but the tissue has mild atrophy; the liver lumen has become narrowed and curved; there are no localized abnormal pictures inside the liver; biopsy of liver cells revealed pictures of mild hepatocirrhosis and chronic hepatitis.

Examinations on liver functions: As Table 1 shows, examinations and observations were done 5 times during a period of about 3 months extending from May 25 to July 30. The first medical examination revealed abnormalities in 5 items—an icterus index, GOT, GPT, LAP, and $\gamma$-GTP—among 13 items.

Treatment with pronase: Empynase (trade name; manufactured by Kaken Chemical Co., Ltd.; enteric preparation; one tablet contains 9,000 tyrosine unit of pronase) was internally administered in a dosage of 6 tablets daily, 2 tablets each after meals, starting on May 25. Examinations were made on June 5. Mild exacerbation was seen in every item in addition to the observation of an abnormal value ot TTT.

Sudden improvements were seen on June 18, only $\gamma$-GTP showing abnormalities. On June 10, $\gamma$-GTP also decreased. On July 30, all showed normal values.

Subjective symptoms improved, too, and results of various examinations became normal. Thereafter, the internal administration was continued for further 3 months for prevention of recurrence.

TABLE 1

Course of results of examinations on liver functions

| Items examined | Normal value | 5/25 day 0 | 6/5 day 10 | 6/18 day 23 | 7/10 day 45 | 7/30 day 65 |
|---|---|---|---|---|---|---|
| Icterus index | 4–6 | *7 | *7 | 4 | 5 | 5 |
| TTT | 0.4–4.0 | 4 | *8 | 1.5 | 1.9 | 1.9 |
| ZTT | 4.0–12.0 | 8.6 | 10.5 | 7.4 | 7.6 | 6.7 |
| GOT | 8–40 | *55 | *95 | 33 | 26 | 20 |
| GPT | 5–35 | *36 | *64 | 26 | 27 | 20 |
| AL-P | 2.0–10.0 | 5.1 | 6.7 | 4.7 | 5.1 | 4.2 |
| LDH | 50–450 | 380 | 342 | 317 | 322 | 308 |
| LAP | 70–200 | *288 | *310 | 190 | 166 | 145 |
| $\gamma$-GTP | –40 | *284 | *251 | *139 | *59 | 38 |
| Total cholesterol | 130–230 | 191 | 218 | 186 | 188 | 175 |
| Total proteins | 6.5–8.3 | 7.6 | 7.5 | 6.8 | 7.5 | 7.1 |
| Albumin | 56–68 | 59.2 | 61.3 | 61.7 | 62.6 | 63.3 |
| A/G | 1.27–2.12 | 1.45 | 1.58 | 1.61 | 1.61 | 1.73 |

*abnormal value

CLINICAL EXAMPLE 2 female; born in 1915

Diagnosis: chronic hepatitis

Chief compaint: general fatigue, anorexia

Present illness: Since about 6 months ago, the patient has complained of general fatigue and anorexia and lost her vigor to work.

Present condition: The patient's face is somewhat pale with a shade of yellow. The patient has an enlarged abdominal part, which has no abnormalities such as retention of ascites.

Ultrasonography and rowentogenography: The kidneys on both sides and the spleen have no abnormalities. The gallbladder has mild hypertrophy but contains no gallstone. There are no significant changes in the pancreas, the large intestine, the small intestine, the stomach, and the duodenum.

Liver: The surface is smooth. The liver lumen has become somewhat narrowed but no atrophy or localized abnormal pictures are observed in the liver tissue.

Examinations on liver functions: As Table 2 shows, examinations that had been carried out on November 7 revealed no abnormalities in 6 items among 13 ones.

TABLE 2

Course of results of examinations on liver functions

| Items examined | 11/7 day 0 | 1/30 next year day 85 | 3/5 day 119 | 5/18 day 193 | 6/5 day 211 |
|---|---|---|---|---|---|
| Icterus index | 4 | 5 | 6 | 4 | 4 |
| TTT | *6.1 | *7.4 | *5.4 | *5.0 | 3.8 |
| ZTT | *13.9 | *12.8 | *12.6 | 7.8 | 7.5 |
| GOT | *59 | *45 | 36 | 31 | 31 |
| GPT | *47 | *39 | 28 | 25 | 24 |
| AL-P | 6.6 | 8.1 | 5.7 | 5.5 | 5.3 |
| LDH | 411 | 356 | 385 | 323 | 320 |
| LAP | 165 | 153 | 151 | 127 | 120 |
| $\gamma$-GTP | *54 | 38 | 34 | 20 | 20 |
| Total cholesterol | 209 | 187 | 210 | 207 | 208 |
| Total proteins | *8.6 | *8.4 | 8.0 | 8.1 | 8.1 |
| Albumin | 58.1 | 57.1 | 57.5 | *55.5 | 57 |
| A/G | 1.38 | 1.33 | 1.35 | *1.25 | 1.28 |

*abnormal value

Treatment with pronase: Empynase P was internally administered in a dosage of 6 tablets daily, 2 tablets each after meals, and the subsequent course observed. On January 30 the next year, $\gamma$-GTP became normal but the others, though somewhat ameliorating, did not be restored to normal. On March 5, all except TTT and ZTT became normal. On May 18, TTT, albumin, and A/G showed abnormalities, but albumin and A/G were low. On June 6. all became normal. This is 2/3 days after the start of the treatment.

Clinical examples 3–7: Treatment of liver disorders with pronase. Each case received internally Empynase P in a dosage of 6 tablets daily.

TABLE 3

| Clinical case | Disease | Sex Age | Number of items examined of abnormal liver functions Before treatment | After treatment | Days of Administration | Effect |
|---|---|---|---|---|---|---|
| 3 | hepatocirrhosis | male 58 | 5 | 0 | 65 | markedly effective |
| 4 | chronic hepatitis | female 67 | 6 | 0 | 213 | markedly effective |
| 5 | chronic hepatitis | male 56 | 5 | 0 | 35 | markedly effective |
| 6 | chronic hepatitis | male 57 | 7 | 3 | 24 | effective |
| 7 | chronic hepatitis | male 57 | 3 | 1 | 59 | " |

As Table 3 further shows, Empynase P was internally administered to 1 case of hepatocirrhosis and 4 cases of chronic hepatitis; as a result, very favorable results were obtained in these cases that had been considered difficult to treat.

CLINICAL EXAMPLE 8 male, born in 1930
Diagnosis: chronic glomerulonephritis
Chief complaint: general fatigue
Present illness: The patient has occasionally complained of general fatigue and facial edema since 5–6 years ago. Examinations that had been carried out a week before the patient visited the hospital revealed proteins in urine and the elevated blood pressure.
Present condition: The patient is of average build and moderately-nourished. His face is somewhat pale and a little edematous. His tonsil has become somewhat enlarged. His blood pressure is 160/89.
Urinalysis: Proteins in urine is 1.3 g a day.
Urinary sediment: In urine: hyaline cast (+); granular cast (+); leukocyte cast (+) red cell cast (+); microscopic hematuria (+)
Blood chemistry: Blood urea nitrogen is normal.
Renal function tests: GFR is 48 ml/min. The concentration test reveals somewhat low values and hence renal functions somewhat decreases. The patient was referred to Osaka Univesity Hospital as having chronic glomerulonephritis. At the hospital, biopsy of the kidneys revealed mild degeneration in the glomeruli and the parenchyma of the kidneys.
Treatment with pronase: Empynase was internally adminstered in a dosage of 6 tablets daily, 2 tablets each after meals, starting on August 20. On September 30, the blood pressure was 152/87 and proteins in urine 1.0 g a day.

Urinary sediment: red cell cast (−); microscopic hematuria (−) On October 30, the blood pressure was 148/82 and proteins in urine 0.7 g a day.
Urinary sediment: There was only hyaline cast in urine.
On December 26, the blood pressure was 142/80 and proteins in urine 0.3 g a day; urinary sediment; a small amount of hyaline cast.
On February 26 next year, the blood pressure was 136/75 and proteins in urine 0; urinary sediment: none. Biopsy of the kidneys that had again been carried out at Osaka University Hospital revealed no abnormalities in the glomeruli and the parenchyma of the kidneys. The treatment, carried out for about 6 months, mostly cured chronic glomerulo-nephritis that had been considered difficult to cure.

CLINICAL EXAMPLE 9 male, born in 1932
Diagnosis: nephrotic syndrome
Chief complaint: anorexia; asthenia
Present illness: The patient has complained of anorexia and asthenia since a half year ago but has been left untreated. Health checking revealed proteinuria.
Present condition: The patient is of average build and moderately-nourished. He has facial edema and a blood pressure of 163/92.
Urinalysis: The amount of proteins excreted in urine is as large as 3.8 g/day.
Urinary sediment: There were observed granular cast, hyaline cast, and fatty cast. There was observed anisotropic lipoid especially in this case. The patient was referred to the Osaka Prefectural Adult Disease Center and there, on various examinations, diagnosed as having nephrotic syndrome.
Treatment with pronase: Empynase was internally administered in a dosage of 6 tablets daily, 2 tablets each after meals, starting on December 8.
On Jananury 14 next year, proteins in urine was reduced to 24 g/day, urinary sediment unchanged, and all kinds of casts recognized.
On Feb. 21, proteins in urine decreased to 1.2 g/day and urinary sediment decreased in general but all kinds of casts were still recognized.
On March 30, proteins in urine was not observed and urinary sediment disappeared.
The patient was mostly cured in 110 days.

EXAMPLE OF ANIMAL EXPERIMENTS

Effects of enzymes on liver disorders were tested. To rats weighing 250 g on the average were intraperitoneally administered 0.5 ml/kg of carbon tetrachloride to induce hepatitis in the animals. Blood was drawn 24 hours later and measured for G.O.T. and G.P.T. that provide indexes for liver disorders. Enzymes were given orally in each dosage on the day of or 6, 5, 2, and 1 days before the administration of carbon tetrachloride. Table 4 summarizes the results. The administration of the enzymes ameliorated the liver disorders.

TABLE 4

| Enzyme Name | Dosage (mg/kg) | Number of rats | Administration of carbon tetrachloride | GOP | GPT |
|---|---|---|---|---|---|
| pronase | 25 | 5 | done | 438 ± 300.5* | 209 ± 179.3 |
| " | 100 | 5 | done | 481 ± 197.1* | 163 ± 81.5* |
| " | 200 | 5 | done | 289 ± 133.0* | 113 ± 97.1* |
|  | 0 | 4 | done | 1291 ± 480.0 | 477 ± 67.8 |
|  | 0 | 4 | not done | 96 ± 25.0 | 23 ± 6.6 |

TABLE 4-continued

| Enzyme | | Number of rats | Administration of carbon tetrachloride | GOP | GPT |
|---|---|---|---|---|---|
| Name | Dosage (mg/kg) | | | | |

The mark * indicates P < 0.05 (by t-test)

What is claimed is:

1. A method of treating chronic hepatitis, chronic glomerulonephritis and nephrotic syndromes in humans and animals which comprises administering to a human or animal in need thereof, a therapeutically effective amount of pronase in combination with a pharmaceutically acceptable carrier.

2. A method according to claim 1 wherein the administration is oral.

3. A method according to claim 2 wherein pronase is orally administered in the form of enteric granules.

* * * * *